US010307250B2

(12) United States Patent
Maimon et al.

(10) Patent No.: US 10,307,250 B2
(45) Date of Patent: Jun. 4, 2019

(54) SYSTEM AND METHOD FOR CRIMPING A PROSTHETIC HEART VALVE

(71) Applicant: Edwards Lifesciences Corporation, Irvine, CA (US)

(72) Inventors: David Maimon, Haifa (IL); Ron Sharoni, Hadera (IL); Tamir S. Levi, Moshav Ein HaEmek (IL); Emil Karapetian, Huntington Beach, CA (US); Tri D. Tran, Fountain Valley, CA (US); Tung T. Le, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 683 days.

(21) Appl. No.: 15/063,319

(22) Filed: Mar. 7, 2016

(65) Prior Publication Data
US 2016/0184096 A1 Jun. 30, 2016

Related U.S. Application Data

(63) Continuation of application No. 14/665,677, filed on Mar. 23, 2015, now Pat. No. 9,277,992, which is a
(Continued)

(51) Int. Cl.
B21D 39/04 (2006.01)
A61F 2/24 (2006.01)
(Continued)

(52) U.S. Cl.
CPC ............ *A61F 2/2427* (2013.01); *A61B 17/06* (2013.01); *A61B 50/30* (2016.02); *A61F 2/0095* (2013.01);
(Continued)

(58) Field of Classification Search
CPC ................... A61F 2/243; A61F 2/0095; A61F 2002/9522; A61B 17/06; A61B 50/30;
(Continued)

(56) References Cited

U.S. PATENT DOCUMENTS 1,438,681 A 12/1922 Bath
2,974,367 A 3/1961 Doering et al.
(Continued)

FOREIGN PATENT DOCUMENTS

DE 19532846 A1 3/1997
DE 19546692 A1 6/1997
(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3 pp. 305-311. 1989.
(Continued)

Primary Examiner — David B Jones
(74) Attorney, Agent, or Firm — Thomas C. Richardson

(57) ABSTRACT

A device for crimping a radially expandable and collapsible prosthetic valve comprises a coiled wire frame having a longitudinal opening extending from a proximal end to a distal end thereof. The opening has a first state and a second state, the opening in the first state having a first diameter dimensioned to receive the prosthetic valve in an expanded or partially crimped configuration therein, and the opening in the second state having a second diameter dimensioned to receive the prosthetic valve in a crimped configuration. The coiled wire frame has a first end coupled to a first member and a second end coupled to a second member. The first
(Continued)

member is movable relative to the second member to convert the coiled wire frame from the first state to the second state.

20 Claims, 10 Drawing Sheets

Related U.S. Application Data continuation of application No. 14/181,425, filed on Feb. 14, 2014, now Pat. No. 8,986,320, which is a continuation of application No. 13/715,605, filed on Dec. 14, 2012, now Pat. No. 8,652,145.

(60) Provisional application No. 61/570,517, filed on Dec. 14, 2011.

(51) Int. Cl.
| | |
|---|---|
| B21D 41/04 | (2006.01) |
| A61B 50/30 | (2016.01) |
| A61B 17/06 | (2006.01) |
| B23P 11/00 | (2006.01) |
| B21D 41/00 | (2006.01) |
| A61F 2/00 | (2006.01) |
| B25B 27/10 | (2006.01) |
| B23P 19/04 | (2006.01) |
| A61F 2/95 | (2013.01) |

(52) U.S. Cl.
CPC ............ *A61F 2/243* (2013.01); *A61F 2/2433* (2013.01); *B21D 41/00* (2013.01); *B21D 41/04* (2013.01); *B23P 11/00* (2013.01); *B23P 19/04* (2013.01); *B25B 27/10* (2013.01); *A61F 2002/9522* (2013.01); *Y10T 29/5367* (2015.01); *Y10T 29/53552* (2015.01); *Y10T 29/53578* (2015.01)

(58) Field of Classification Search
CPC .......... B21D 41/00; B23P 11/00; B23P 19/04; B25B 27/10
USPC .......................................................... 72/402
See application file for complete search history.

(56) References Cited

U.S. PATENT DOCUMENTS

| | | |
|---|---|---|
| 3,755,823 A | 9/1973 | Hancock |
| 4,035,849 A | 7/1977 | Angell et al. |
| 4,777,951 A | 10/1988 | Cribier et al. |
| 4,787,899 A | 11/1988 | Lazarus |
| 4,796,629 A | 1/1989 | Grayzel |
| 4,856,516 A | 8/1989 | Hillstead |
| 4,878,495 A | 11/1989 | Grayzel |
| 4,966,604 A | 10/1990 | Reiss |
| 4,994,077 A | 2/1991 | Dobben |
| 5,059,177 A | 10/1991 | Towne et al. |
| 5,192,297 A | 3/1993 | Hull |
| 5,282,847 A | 2/1994 | Trescony et al. |
| 5,370,685 A | 12/1994 | Stevens |
| 5,411,552 A | 5/1995 | Andersen et al. |
| 5,545,214 A | 8/1996 | Stevens |
| 5,554,185 A | 9/1996 | Block et al. |
| 5,558,644 A | 9/1996 | Boyd et al. |
| 5,584,803 A | 12/1996 | Stevens et al. |
| 5,591,195 A | 1/1997 | Taheri et al. |
| 5,607,464 A | 3/1997 | Trescony et al. |
| 5,626,604 A | 5/1997 | Cottone, Jr. |
| 5,665,115 A | 9/1997 | Cragg |
| 5,749,921 A | 5/1998 | Lenker et al. |
| 5,769,812 A | 6/1998 | Stevens et al. |
| 5,800,508 A | 9/1998 | Goicoechea et al. |
| 5,810,873 A | 9/1998 | Morales |
| 5,836,952 A | 11/1998 | Davis et al. |
| 5,840,081 A | 11/1998 | Andersen et al. |
| 5,855,597 A | 1/1999 | Jayaraman |
| 5,925,063 A | 7/1999 | Khosravi |
| 5,992,000 A | 11/1999 | Humphrey et al. |
| 6,027,525 A | 2/2000 | Suh et al. |
| 6,082,990 A | 7/2000 | Jackson et al. |
| 6,168,614 B1 | 1/2001 | Andersen et al. |
| 6,221,091 B1 | 4/2001 | Khosravi |
| 6,245,102 B1 | 6/2001 | Jayaraman |
| 6,302,906 B1 | 10/2001 | Goecoechea et al. |
| 6,309,383 B1 | 10/2001 | Campbell et al. |
| 6,360,577 B2 | 3/2002 | Austin |
| 6,425,916 B1 | 7/2002 | Garrison et al. |
| 6,454,799 B1 | 9/2002 | Schreck |
| 6,458,153 B1 | 10/2002 | Bailey et al. |
| 6,461,382 B1 | 10/2002 | Cao |
| 6,482,228 B1 | 11/2002 | Norred |
| 6,527,979 B2 | 3/2003 | Constantz |
| 6,558,418 B2 | 5/2003 | Carpentier et al. |
| 6,582,462 B1 | 6/2003 | Andersen et al. |
| 6,618,921 B1 | 9/2003 | Thornton |
| 6,629,350 B2 | 10/2003 | Motsenbocker |
| 6,651,478 B1 | 11/2003 | Kokish |
| 6,652,578 B2 | 11/2003 | Bailey et al. |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,823,576 B2 | 11/2004 | Austin |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,915,560 B2 | 7/2005 | Austin |
| 6,920,674 B2 | 7/2005 | Thornton |
| 6,925,847 B2 | 8/2005 | Motsenbocker |
| 6,931,899 B2 | 8/2005 | Goff et al. |
| 6,968,607 B2 | 11/2005 | Motsenbocker |
| 6,988,881 B2 | 1/2006 | Motsenbocker et al. |
| 7,010,953 B2 | 3/2006 | Stupecky |
| 7,018,406 B2 | 3/2006 | Seguin et al. |
| 7,018,408 B2 | 3/2006 | Bailey et al. |
| 7,021,114 B2 | 4/2006 | Perreault |
| 7,069,794 B2 | 7/2006 | Motsenbocker et al. |
| 7,096,554 B2 | 8/2006 | Austin et al. |
| 7,143,625 B2 | 12/2006 | Edin |
| 7,207,204 B2 | 4/2007 | Weber et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,415,861 B2 | 8/2008 | Sokel |
| 7,462,191 B2 | 12/2008 | Spenser et al. |
| 7,487,579 B2 | 2/2009 | Eidenschink et al. |
| 7,510,575 B2 | 3/2009 | Spenser et al. |
| 7,530,253 B2 | 5/2009 | Spenser et al. |
| 7,585,321 B2 | 9/2009 | Cribier |
| 7,587,801 B2 | 9/2009 | Austin |
| 7,618,446 B2 | 11/2009 | Andersen et al. |
| 7,655,034 B2 | 2/2010 | Mitchell et al. |
| 7,749,266 B2 | 7/2010 | Forster et al. |
| 7,785,366 B2 | 8/2010 | Maurer et al. |
| 7,895,876 B2 | 3/2011 | Spenser et al. |
| 7,959,672 B2 | 6/2011 | Salahieh et al. |
| 7,967,138 B2 | 6/2011 | Ryan et al. |
| 7,993,394 B2 | 8/2011 | Hariton et al. |
| 8,006,535 B2 | 8/2011 | Righini et al. |
| 8,029,556 B2 | 10/2011 | Rowe |
| 8,112,857 B2 | 2/2012 | Voelkl |
| 8,167,932 B2 | 5/2012 | Bourang |
| 8,182,530 B2 | 5/2012 | Huber |
| 8,312,614 B2 | 11/2012 | Sokel |
| 8,449,606 B2 | 5/2013 | Eliasen et al. |
| 8,652,145 B2* | 2/2014 | Maimon ................. B21D 41/04 206/370 |
| 9,155,619 B2 | 10/2015 | Liu et al. |

(56) References Cited

U.S. PATENT DOCUMENTS

| | | | |
|---|---|---|---|
| 9,168,131 B2 | 10/2015 | Yohanan et al. | |
| 9,277,992 B2* | 3/2016 | Maimon | B21D 41/04 |
| 9,867,700 B2 | 1/2018 | Bakis et al. | |
| 2002/0026094 A1 | 2/2002 | Roth | |
| 2002/0032481 A1 | 3/2002 | Gabbay | |
| 2002/0138135 A1 | 9/2002 | Duerig et al. | |
| 2002/0161377 A1 | 10/2002 | Rabkin | |
| 2003/0040792 A1 | 2/2003 | Gabbay | |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2004/0186563 A1 | 9/2004 | Lobbi | |
| 2004/0186565 A1 | 9/2004 | Schreck | |
| 2004/0210304 A1 | 10/2004 | Seguin et al. | |
| 2004/0236411 A1 | 11/2004 | Sarac et al. | |
| 2004/0260389 A1 | 12/2004 | Case et al. | |
| 2005/0075731 A1 | 4/2005 | Artof et al. | |
| 2005/0096736 A1 | 5/2005 | Osse et al. | |
| 2005/0113910 A1 | 5/2005 | Paniagua et al. | |
| 2005/0137688 A1 | 6/2005 | Salahieh et al. | |
| 2005/0137693 A1 | 6/2005 | Haug et al. | |
| 2005/0137697 A1 | 6/2005 | Salahieh et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0025857 A1 | 2/2006 | Bergheim et al. | |
| 2006/0058872 A1 | 3/2006 | Salahieh et al. | |
| 2006/0149350 A1 | 7/2006 | Patel et al. | |
| 2006/0149360 A1 | 7/2006 | Schwammenthal et al. | |
| 2006/0213049 A1 | 9/2006 | Serrano et al. | |
| 2006/0259136 A1 | 11/2006 | Nguyen et al. | |
| 2006/0276813 A1 | 12/2006 | Greenberg | |
| 2006/0287719 A1 | 12/2006 | Rowe et al. | |
| 2007/0005131 A1 | 1/2007 | Taylor | |
| 2007/0010877 A1 | 1/2007 | Salahieh et al. | |
| 2007/0056346 A1 | 3/2007 | Spenser et al. | |
| 2007/0073389 A1 | 3/2007 | Bolduc et al. | |
| 2007/0088431 A1 | 4/2007 | Bourang et al. | |
| 2007/0112422 A1 | 5/2007 | Dehdashtian | |
| 2007/0203503 A1 | 8/2007 | Salahieh et al. | |
| 2007/0203575 A1 | 8/2007 | Forster et al. | |
| 2007/0213813 A1 | 9/2007 | Von Segesser et al. | |
| 2007/0265700 A1 | 11/2007 | Eliasen et al. | |
| 2008/0114442 A1 | 5/2008 | Mitchell et al. | |
| 2008/0125853 A1 | 5/2008 | Bailey et al. | |
| 2008/0319526 A1 | 12/2008 | Hill et al. | |
| 2009/0043249 A1 | 2/2009 | Sokel | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0319037 A1 | 12/2009 | Rowe et al. | |
| 2010/0049313 A1 | 2/2010 | Alon et al. | |
| 2010/0191326 A1 | 7/2010 | Alkhatib | |
| 2010/0198347 A1 | 8/2010 | Zakay et al. | |
| 2011/0015729 A1 | 1/2011 | Jimenez et al. | |
| 2011/0040374 A1 | 2/2011 | Goetz et al. | |
| 2011/0295216 A1* | 12/2011 | Miller | A61F 2/2436 604/264 |
| 2012/0071969 A1 | 3/2012 | Li et al. | |
| 2012/0123529 A1 | 5/2012 | Levi et al. | |
| 2012/0239142 A1 | 9/2012 | Liu et al. | |
| 2013/0023985 A1 | 1/2013 | Khairkhahan et al. | |
| 2013/0317598 A1 | 11/2013 | Rowe et al. | |
| 2014/0331475 A1* | 11/2014 | Duffy | A61F 2/243 29/446 |
| 2015/0157455 A1 | 6/2015 | Hoang et al. | |
| 2017/0056149 A1 | 3/2017 | Rajpara et al. | |
| 2017/0128197 A1 | 5/2017 | Bialas et al. | |
| 2017/0156839 A1 | 6/2017 | Cooper et al. | |
| 2017/0156859 A1 | 6/2017 | Chang et al. | |
| 2017/0231765 A1 | 8/2017 | Desrosiers et al. | |
| 2017/0258584 A1 | 9/2017 | Chang et al. | |

FOREIGN PATENT DOCUMENTS

| | | |
|---|---|---|
| DE | 19857887 A1 | 7/2000 |
| DE | 19907646 A1 | 8/2000 |
| EP | 0103546 A1 | 3/1984 |
| EP | 0592410 A1 | 4/1994 |
| EP | 0597967 A1 | 5/1994 |
| EP | 0850607 A1 | 7/1998 |
| EP | 1796597 A2 | 6/2007 |
| EP | 2704668 B1 | 6/2016 |
| FR | 2788217 A1 | 7/2000 |
| FR | 2815844 A1 | 5/2002 |
| SU | 1271508 A1 | 11/1986 |
| WO | 91/17720 A1 | 11/1991 |
| WO | 1993001768 A1 | 2/1993 |
| WO | 98/29057 A1 | 7/1998 |
| WO | 1999040964 A1 | 8/1999 |
| WO | 1999047075 A1 | 9/1999 |
| WO | 01/49213 A2 | 7/2001 |
| WO | 0154625 A1 | 8/2001 |
| WO | 01/76510 A2 | 10/2001 |
| WO | 02/22054 A1 | 3/2002 |
| WO | 02/36048 A1 | 5/2002 |
| WO | 02/47575 A2 | 6/2002 |
| WO | 0347468 A1 | 6/2003 |
| WO | 2005034812 A1 | 4/2005 |
| WO | 2005084595 A1 | 9/2005 |
| WO | 2005102015 A2 | 11/2005 |
| WO | 2006111391 A1 | 10/2006 |
| WO | 2006/138173 A2 | 12/2006 |
| WO | 2007047488 A2 | 4/2007 |
| WO | 2007067942 A1 | 6/2007 |
| WO | 2007097983 A2 | 8/2007 |
| WO | 2008/005405 A2 | 1/2008 |
| WO | 2008091515 A2 | 7/2008 |
| WO | 2009033469 A1 | 3/2009 |
| WO | 2010121076 A2 | 10/2010 |

OTHER PUBLICATIONS

Bailey, S. "Percutaneous Expandable Prosthetic Valves," Textbook of Interventional Cardiology vol. 2, 2nd Ed. pp. 1268-1276. 1994.

H.R. Andersen "History of Percutaneous Aortic Valve Prosthesis," Herz No. 34. pp. 343-346. 2009.

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Uchida, "Modifications of Gianturco Expandable Wire Stents," American Journal of Roentgenology, vol. 150. pp. 1185-1187. 1986.

Wheatley, "Valve Prostheses," Operative Surgery, 4th ed. pp. 415-424. 1986.

* cited by examiner

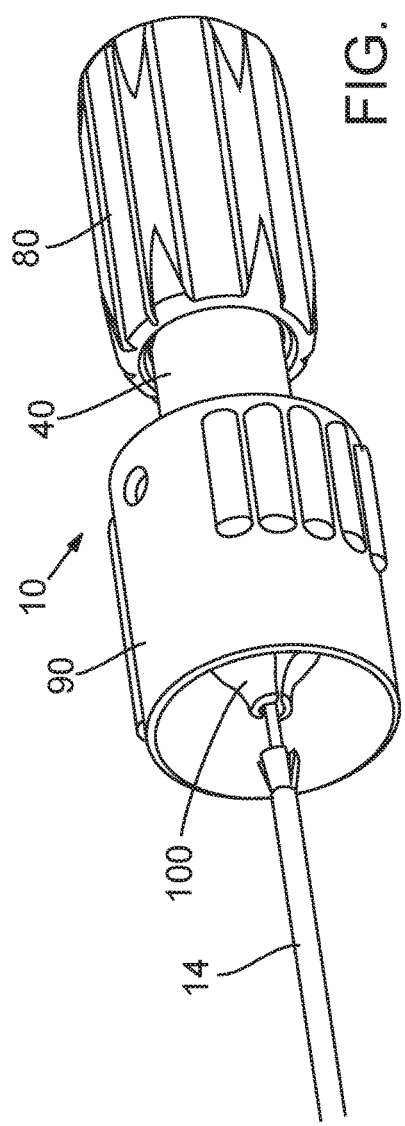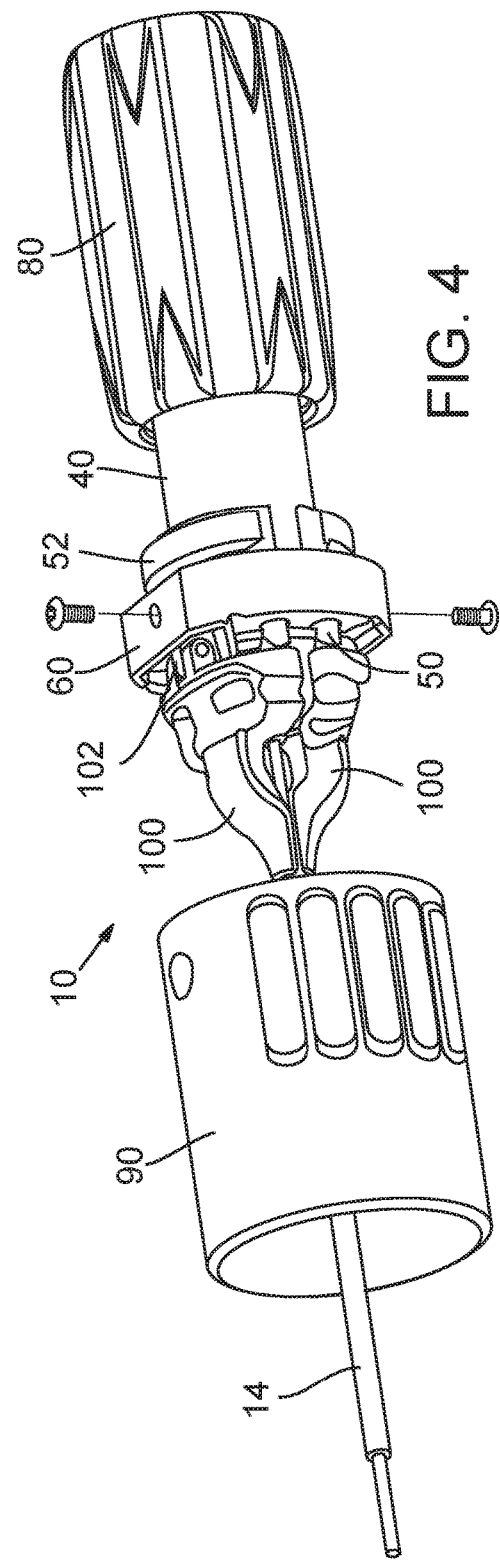

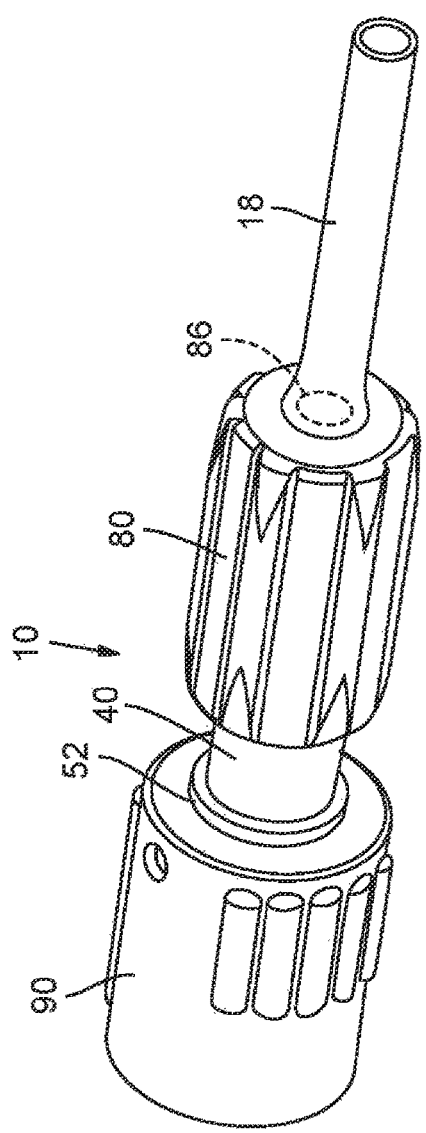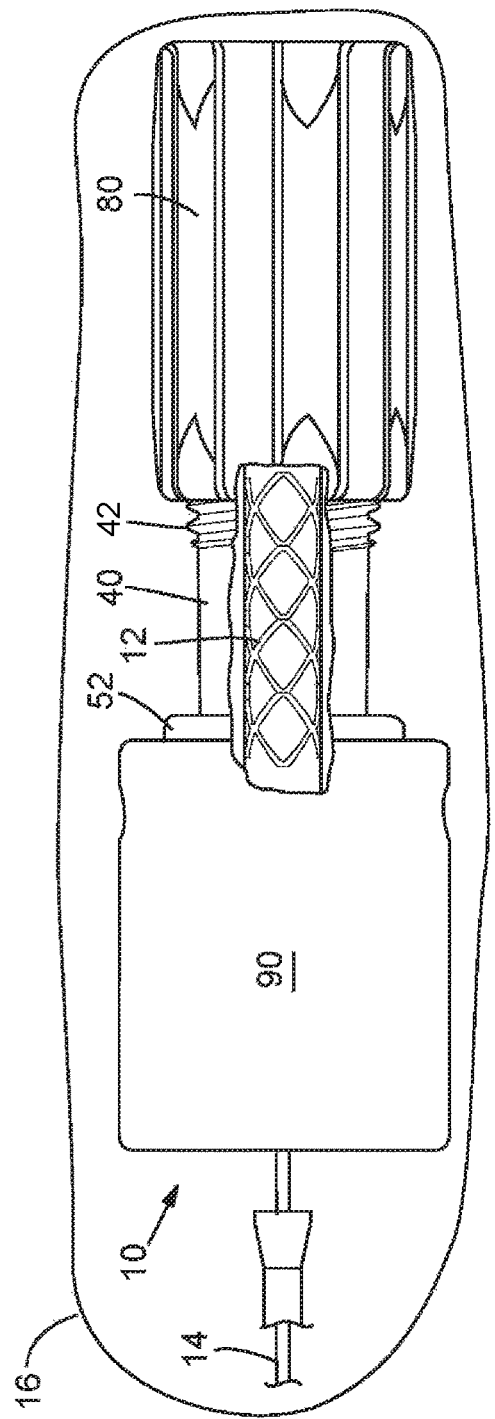

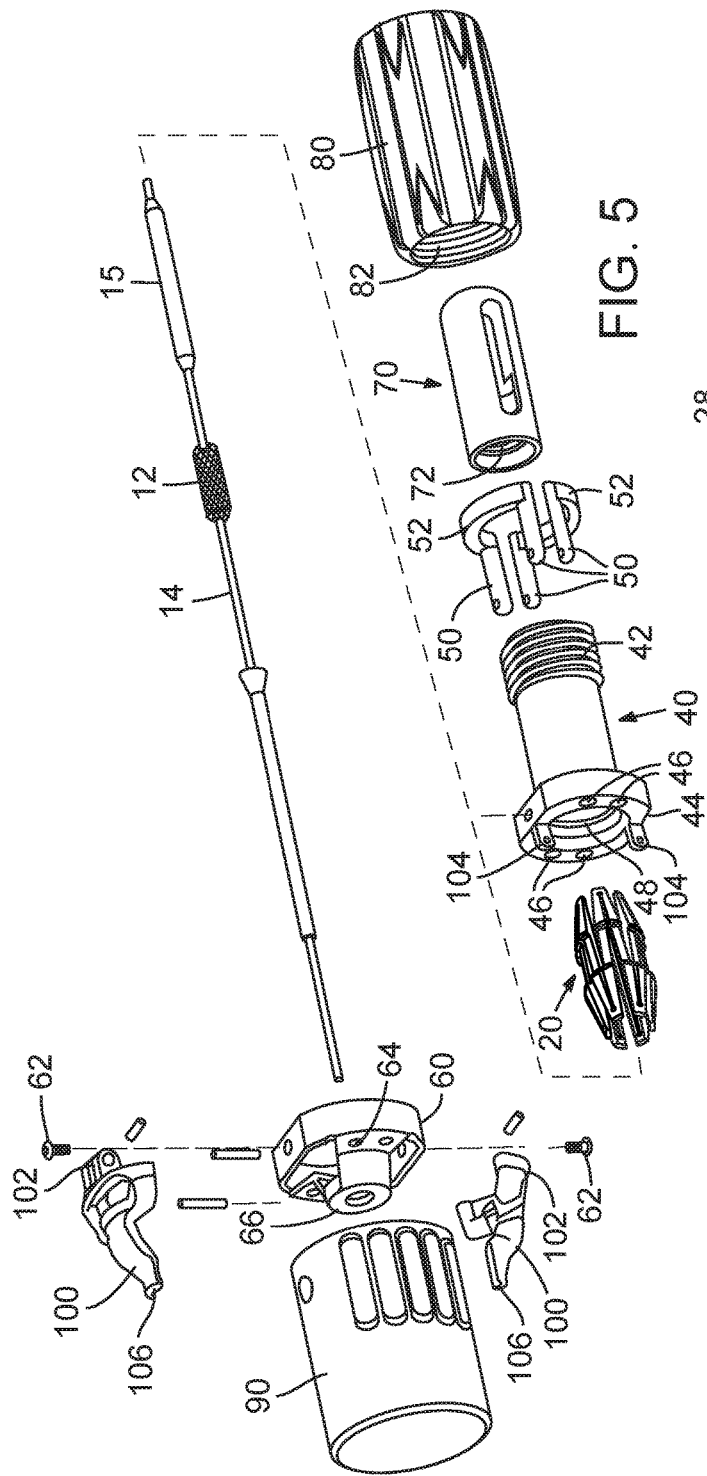

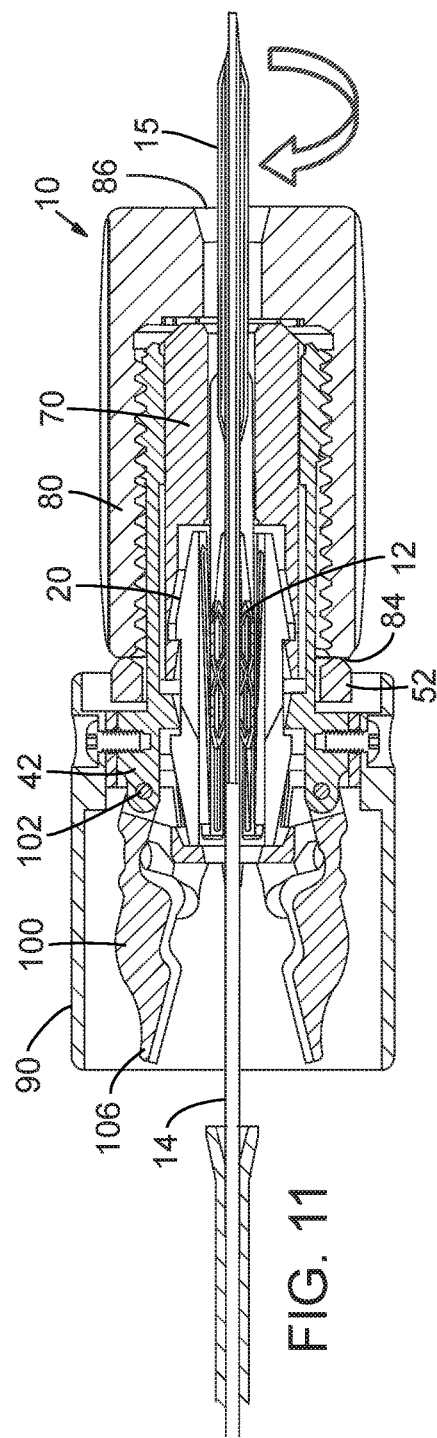
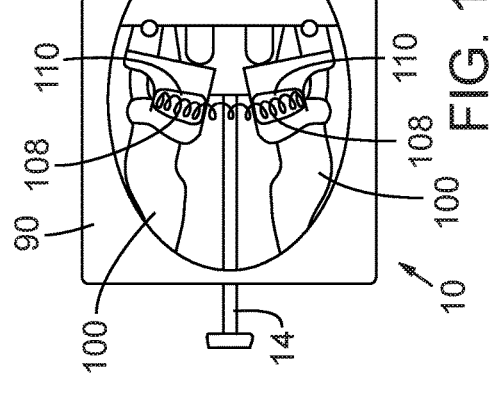
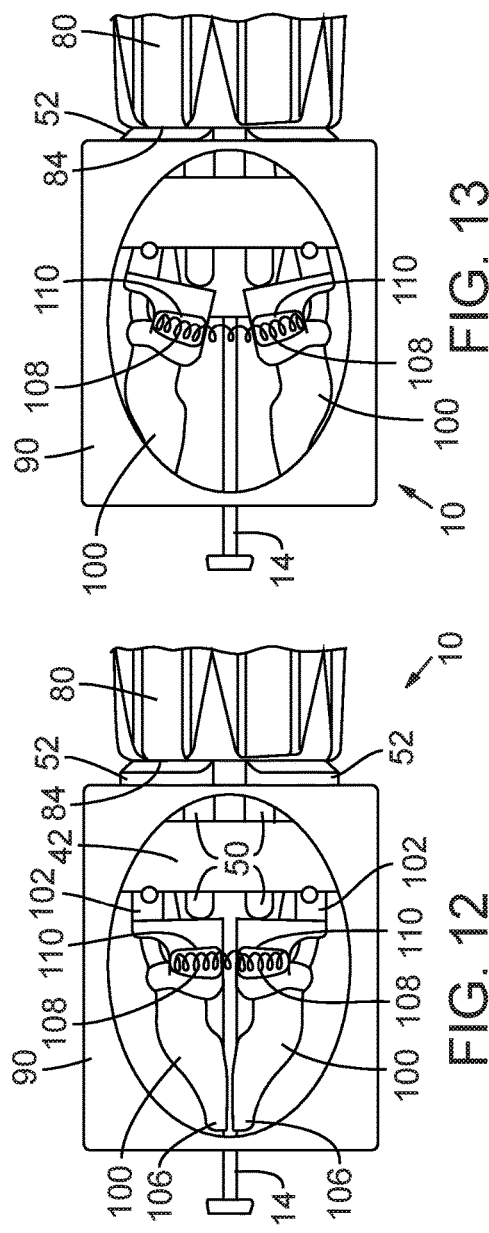

SYSTEM AND METHOD FOR CRIMPING A PROSTHETIC HEART VALVE

CROSS-REFERENCE TO RELATED APPLICATIONS

This application is a continuation of U.S. patent application Ser. No. 14/665,677, filed Mar. 23, 2015, which is a continuation of U.S. patent application Ser. No. 14/181,425, filed Feb. 14, 2014, now U.S. Pat. No. 8,986,320, which is a continuation of U.S. patent application Ser. No. 13/715,605, filed Dec. 14, 2012, now U.S. Pat. No. 8,652,145, which claims the benefit of U.S. Patent Application No. 61/570,517, filed Dec. 14, 2011, the entire disclosures of which are incorporated by reference.

FIELD

This disclosure relates to systems and methods for crimping a prosthetic valve for delivery into a body.

SUMMARY

Disclosed herein are embodiments of systems and devices for crimping a prosthetic valve, and related methods. Some exemplary systems comprise a radially expandable and compressible prosthetic valve, a crimping device positioned around the valve and configured to reduce the diameter of the valve to a delivery configuration, and a sterile package enclosing the valve and the crimping device. The valve can be pre-assembled in a partially crimped configuration within the crimping device. After removing the sterile packaging, the crimping device can be used to crimp the valve from the partially crimped configuration to the delivery configuration, such as by twisting a knob on the crimping device. The system can further comprise at least a portion of a delivery catheter within the sterile package, wherein the valve is pre-mounted on or adjacent to an inflatable balloon of the delivery catheter, and the valve is crimped onto the delivery catheter using the crimping device.

The crimping device can comprise a radially compressible collet positioned around the valve and a rotatable knob coupled to the collet, wherein rotation of the knob causes radial compression of the collet and crimping of the valve. The crimping device can further comprise a releasable holding mechanism configured to releasably grip a shaft of a delivery catheter to maintain a position of the crimping device relative to the shaft.

Some embodiments of the system can further comprise a loader coupled to an end of the crimping device within the sterile package. The loader can be configured to receive the valve, in the delivery configuration, from the crimping device. In some embodiments, the loader can be separately coupled to the crimping device after the device is removed from the package.

Some embodiments of a crimping device comprise a radially compressible collet configured to house a prosthetic valve and comprising a first axial end portion, an opposing second axial end portion, and an intermediate portion between the first and second axial end portions. The first and second axial end portions are each tapered from a greater outer diameter adjacent to the intermediate portion to a lesser outer diameter proximate the respective axial ends of the collet. The device further comprises a mechanism for radially compressing the collet in order to crimp the valve onto a delivery catheter. The collet can be configured to receive a prosthetic valve in a partially crimped configuration, and the mechanism can be configured to crimp the valve from the partially crimped configuration to a delivery configuration. The intermediate portion of the collet can have an outer diameter that is less than the outer diameter of the first and second axial end portions immediately adjacent to the intermediate portion. The collet can comprise a plurality of elongated members positioned side-by-side in a cylindrical arrangement, with each elongated member being connected to a first neighboring elongated member at a first end and connected to a second neighboring elongated member at a second, opposite end. The device can further comprise a pusher comprising an internally tapered surface that is configured to slide over a corresponding externally tapered surface of the first axial end portion of the collet to compress the collet. The device can further comprise a rotatable knob coupled to the collet such that rotation of the knob causes compression of the collet. In some embodiments, further rotation of the knob in the same direction releases pressure on the collet and allows the collet to expand.

An exemplary method for crimping a prosthetic valve comprises: receiving a prosthetic valve pre-assembled within a crimping device in a sterile package; removing the crimping device and valve from the sterile package; and, using the crimping device, crimping the valve to a delivery configuration onto a delivery catheter. The valve can be pre-assembled within the crimping device in a partially crimped configuration. Crimping the valve can comprise radially compressing the valve from a partially crimped configuration to the delivery configuration with the valve mounted on the delivery catheter, and then releasing compression on the valve from the crimping device. Radially compressing the valve can comprise rotating a knob of the crimping device from a first position to a second position, and releasing compression on the valve can comprise further rotating the knob from the second position to a third position. The method can further comprise releasing the crimping device from the delivery catheter by further rotating the knob from the third position to a fourth position, thereby permitting axial movement of the delivery catheter relative to the crimping device. The method can further comprise advancing the valve out of a distal outlet of the crimping device and directly into a loader. Advancing the valve can comprise coupling the distal outlet of the crimping device to an inlet of the loader that is already coupled to a patient.

The foregoing and other objects, features, and advantages of the invention will become more apparent from the following detailed description, which proceeds with reference to the accompanying figures.

BRIEF DESCRIPTION OF THE DRAWINGS

FIG. 1 is a perspective view of an exemplary valve crimping system disclosed herein.

FIG. 2 is a partial cut-away view of the system of FIG. 1.

FIG. 3 is a perspective view of another exemplary valve crimping system disclosed herein.

FIGS. 4 and 5 are exploded views of the system shown in FIG. 1.

FIGS. 6 and 7 are perspective views of exemplary collets disclosed herein.

FIGS. 8-11 are cross-sectional side views of the exemplary system shown in FIG. 1.

FIGS. 12 and 13 are partial cut-away side views of the system shown in FIG. 1, illustrating an exemplary releasable holding mechanism.

DETAILED DESCRIPTION

Figure 8:
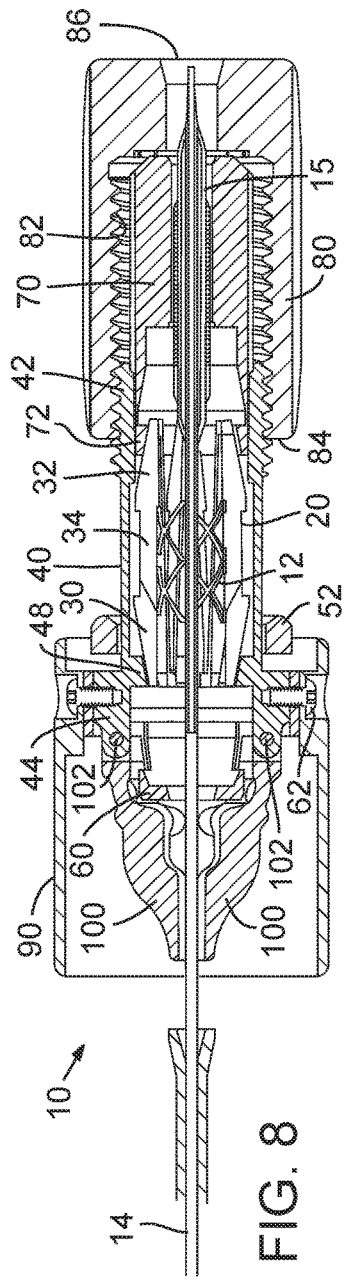

FIGS. 1-3 show exemplary systems for crimping a prosthetic valve and other crimpable, implantable medical devices, such as stents, grafts, etc. The illustrated systems comprise a crimping device 10 and a radially expandable and compressible prosthetic valve 12 positioned within the crimping device. The crimping device 10 is configured to reduce the diameter of the valve 12 to a delivery configuration for delivery into a patient.

The exemplary system shown in FIG. 1 further comprises at least a portion of a delivery catheter 14, such that valve 12 and the crimping device 10 are positioned around and mounted on the delivery catheter 14. The exemplary system shown in FIG. 2 further comprises a sterile package 16 enclosing an assembly comprised of the crimping device 10, the valve 12, and at least a portion of the delivery catheter 14. In another embodiment, the system can comprise the crimping device 10 positioned around the valve 12 and enclosed within the sterile package 16 without any portion of the delivery catheter 14. In some of these embodiments, the delivery catheter 14 can be separately provided within another sterile package and later combined with the crimping device 10 and valve 12 when ready to be used. The exemplary embodiment shown in FIG. 3 further comprises an optional loader 18 coupled to a distal end of the crimping device 10.

These systems can come pre-assembled in a sterile package 16 such that the system can be removed from the package just prior to the crimping device 10 being used to crimp the valve 12 to a delivery configuration onto the delivery catheter 14 and then delivering the valve into a patient. The components can be sealed within the sterile package 16 in a wet state or a dry state. In a wet state, a sterilization fluid can be included within the sterile package 16. In a dry state, the leaflets of the valve 12 (typically made from bovine pericardium tissue or other natural or synthetic tissues) desirably are completely or substantially dehydrated and the package 16 desirably is free of any liquid.

The prosthetic valve 12 can comprise any radially collapsible and expandable prosthetic valve, such as a prosthetic heart valve. The valve 12 can be radially collapsible and expandable between an expanded configuration and a delivery configuration. The valve 12 can be self-expandable or balloon (plastically) expandable. In some embodiments, the valve 12 can be in a partially crimped configuration prior to being assembled within the crimping device 10. For example, the valve can be pre-crimped to the partially crimped configuration using another crimping instrument, prior to being assembled into crimping device 10. In the partially crimped configuration, the valve 12 has an outer diameter that is between that of the expanded configuration and that of the delivery configuration. In some embodiments, the valve 12 can have an outer diameter in the partially crimped configuration that is closer to the outer diameter in the delivery configuration than to the outer diameter in the expanded configuration. For example, the valve 12 in the partially crimped configuration can be crimped about 75% of the way from the expanded configuration to the delivery configuration. The crimping device 10 can also be configured to crimp the valve 12 to the delivery configuration from the expanded configuration without first pre-crimping the valve to an intermediate partially crimped configuration.

After the valve 12 is crimped onto the delivery catheter 14 in the delivery configuration, the valve can be removed from the crimping device 10. In some embodiments, the valve 12 and catheter 14 can be retracted proximally out of and separated from the crimping device 10. In other embodiments, the valve 12 and the delivery catheter 14 can be advanced distally through a distal outlet 86 of the crimping device 10 such that the crimping device remains positioned around a portion of the delivery catheter that is proximal to the valve 12. In other embodiments, the crimping device 10 can be configured to separate into pieces or open, such as like a clam shell, such that the crimping device 10 can be removed laterally from the catheter 14 and valve 12. After the valve 12 is removed from the crimping device 10, the valve and catheter 14 can be introduced into a patient.

FIGS. 4 and 5 show exploded views of the system shown in FIG. 1. As shown in FIG. 6, the crimping device 10 can comprise a collet 20 that is configured to house the valve 12 within the collet. The collet 20 is configured to be resiliently compressible in a radial direction such that radial compression on the collet 20 can cause crimping of the valve 12 positioned within the collet. The collet 20 can further be substantially non-compressible in the axial direction. In the embodiment shown in FIG. 6, the collet 20 comprises a plurality of elongated members 22 positioned side-by-side in a cylindrical arrangement, with each elongated member 22 being connected to a first neighboring elongated member at a first axial end 24 and being connected to a second neighboring elongated member at a second, opposite axial end 26. In an uncompressed state, as shown in FIG. 6, each elongated member 22 can form a first angle $\alpha$ with each of the two adjacent elongated members, and the collet 20 can have a first inner diameter $D_f$. As the collet 20 is radially compressed, the elongated members 22 can pivot towards one another about the axial ends 24, 26, reducing the angle $\alpha$ and reducing the inner diameter $D_f$. FIG. 7 shows an alternative embodiment of the collet 20A that comprises elongated members 28 that are curved along their axial length. The collets 20 or 20A can comprise flexible material, such as metal or plastic, for example HDPE or silicone. In some embodiments, a protective sleeve can be positioned along the internal surface of the collet 20 to protect the valve 12 from damage from the collet during crimping.

As shown in FIG. 6, the collet 20 can comprise a first axial end portion 30, an opposing second axial end portion 32, and an intermediate portion 34 between the first and second axial end portions. The first and second axial end portions 30, 32 are each tapered from a greater outer diameter adjacent the intermediate portion 34 to a lesser outer diameter proximate the respective axial ends of the collet 20. The collet 20 further comprises a pair of opposing step-down portions, or steps, 36, 38 positioned between the intermediate portion 34 and the axial end portions 30, 32, respectively. The intermediate portion 34 of the collet has a reduced outer diameter between the steps 36, 38 that is less than the outer diameter of the first and second axial end portions 30, 32 immediately adjacent to the steps.

As shown in FIG. 5, the crimping device can further comprise a rigid housing 40 within which the collet 20 is positioned. The housing 40 can be generally cylindrical with an externally threaded portion 42 at a distal end and a flared portion 44 at a proximal end.

The crimping device 10 can further comprise a stop 60 that is secured to the flared portion 44 of the housing 40 via a pair of screws 62. The stop 60 can comprise a tapered wall 66 that is configured to restrict the axial position of the collet 20 in the proximal direction relative to the housing 40 and the stop 60. The wall 66 can be configured to match the tapered shape of the proximal end portion 30 of the collet 20.

The crimping device 10 can further comprise a pusher 70 that is generally cylindrical and fits within the distal end 42 of the housing 40. The pusher 70 defines an opening at its proximal end that is configured to receive the distal end portion 32 of the collet 20. As shown in FIG. 8, the pusher 70 comprises an internal annular ledge 72 at its proximal end that is configured to slidably engage the tapered external surface of the distal end portion 32 of the collet 20. As the pusher 70 is urged proximally against the collet 20, the annular ledge 72 imparts axial force in the proximal direction as well as radially inward force against the distal end portion 32 of the collet.

As shown in FIG. 8, the housing 40 can further comprise an internal annular ledge 48 that is configured to slidably engage the tapered external surface of the proximal end portion 30 of the collet. As the pusher 70 moves proximally relative to the housing 40, the internal annular ledges 48 and 72 become closer together and cooperate to pinch the collet 20 between them. As the collet 20 is pinched, the annular ledges 48, 72 slide along the respective axial end portions 30, 32 of the collet toward the intermediate portion 34. This causes the collet 20 to radially compress.

Figure 21A:
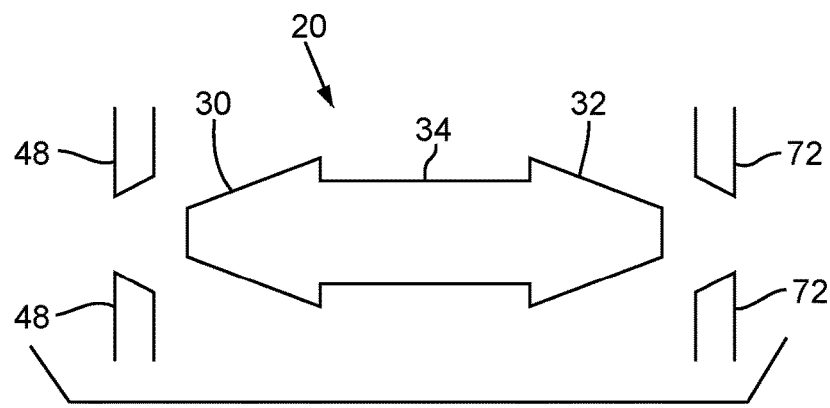
Figure 21B:
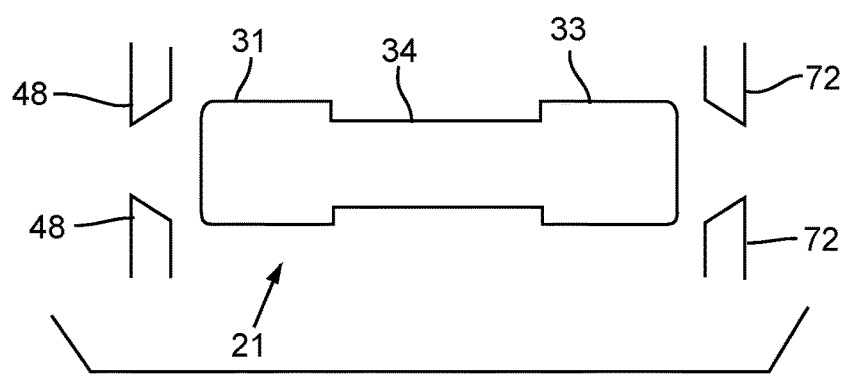
Figure 21C:
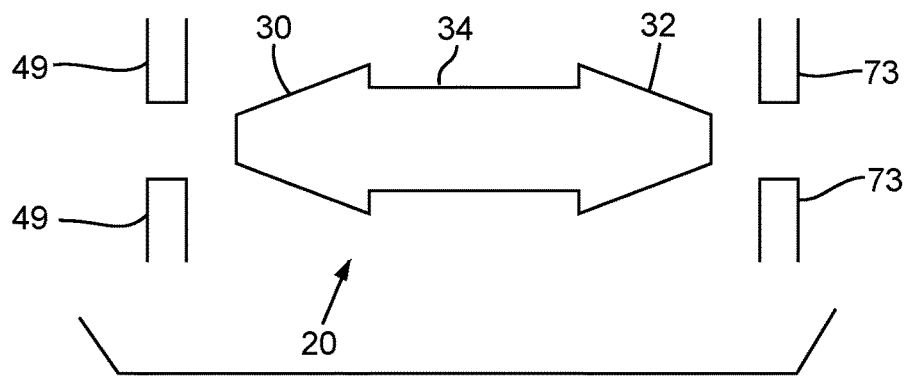

In the embodiment of the crimping device 10 shown in FIG. 8, the end portions 30, 32 of the collet 20 and the internal annular ledges 48, 72 are tapered. This embodiment is shown in FIG. 21A. FIG. 21B shows an alternative embodiment of the crimping device 10 comprising a collet 21 that comprises non-tapered end portions 31 and 33. The non-tapered end portions 31, 33 are still greater in diameter than the intermediate portion 34 of the collet. Even though the end portions 31, 33 are not tapered, because the internal annular ledges 48 and 72 are tapered, the crimping device 10 can still function in the same manner as the embodiment shown in FIG. 21A. FIG. 21C shows yet another alternative embodiment of the crimping device 10 comprising the same collet 20 as in FIG. 21A, but wherein the internal annular ledges 49 and 73 are not tapered. Like with the embodiment of FIG. 21B, the embodiment of FIG. 21C can still function in the same manner as the embodiment of FIG. 21A.

The crimping device 10 can further comprise a rotatable knob 80 that is internally threaded and positioned around and engaged with the externally threaded end portion 42 of the housing 40. The knob 80 can surround the pusher 70 such that axial movement of the knob 80 in the proximal direction causes corresponding axial movement of the pusher 70. The engagement of the inner threads 82 of the knob 80 with the external threads 42 of the housing 40 can be such that rotation of the knob 80 in one direction relative to the housing 40 causes the knob to move proximally relative to the housing. Rotation of the knob 80 in the opposite direction can cause the knob to move distally relative to the housing 40. Thus, rotation of the knob 80 relative to the housing 40 can urge the pusher 70 against the collet 20 thereby pinching the collet between the internal annular ledges 48, 72 and causing the collet to radially compress.

The crimping device 10 can further comprise an external casing 90 that is secured around the proximal flared end 44 of the housing 40. The casing 90 can be fixed relative to the housing 40 and serve as hand grip for a user. The casing 90 can be generally cylindrical and can be secured to the housing 40 and the stop 60 via the screws 62.

The crimping device 10 can further comprise a releasable holding mechanism configured to releasably grip a shaft of a delivery catheter 14 to maintain a position of the crimping device relative to the shaft. An exemplary holding mechanism comprises a pair of clamping jaws 100 that are pivotable about the flared end 44 of the housing 40, as shown in FIGS. 8-13. As shown in FIG. 5, each jaw 100 can comprise a hinge 102 that is pivotally coupled to a tang 104 protruding from the flared end 44 of the housing 40. The jaws 100 further comprise a clamping portion 106 configured to grip onto the delivery catheter 14. A pair of springs, or other similar mechanism, can couple the two jaws 100 together such that they are biased toward each other and a separation force is needed to separate the clamping portions 106 from the delivery catheter 14. For example, FIGS. 12 and 13 show a spring 108 coupled at each end to a spring seat 110 of each jaw 100. The spring 108 is configured to resiliently extend under a separation force to allow the jaws 100 to open, and resiliently contract to reclose the jaws when the separation force is removed.

Figure 9:
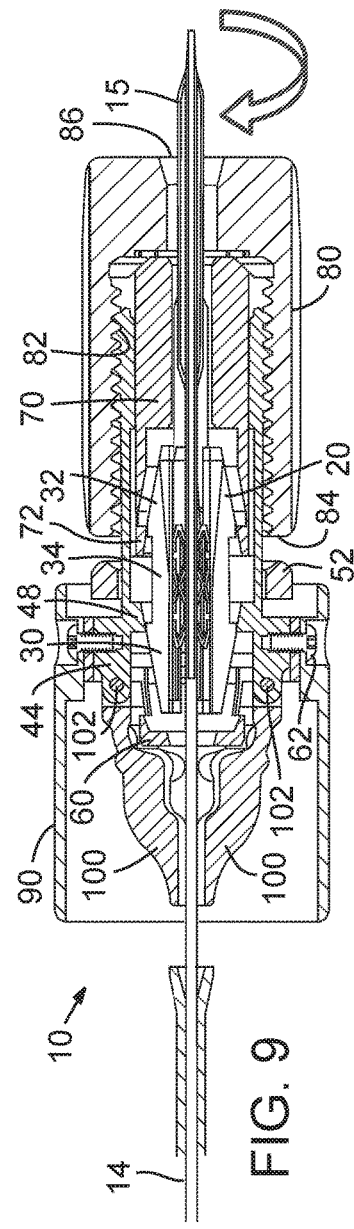
Figure 10:
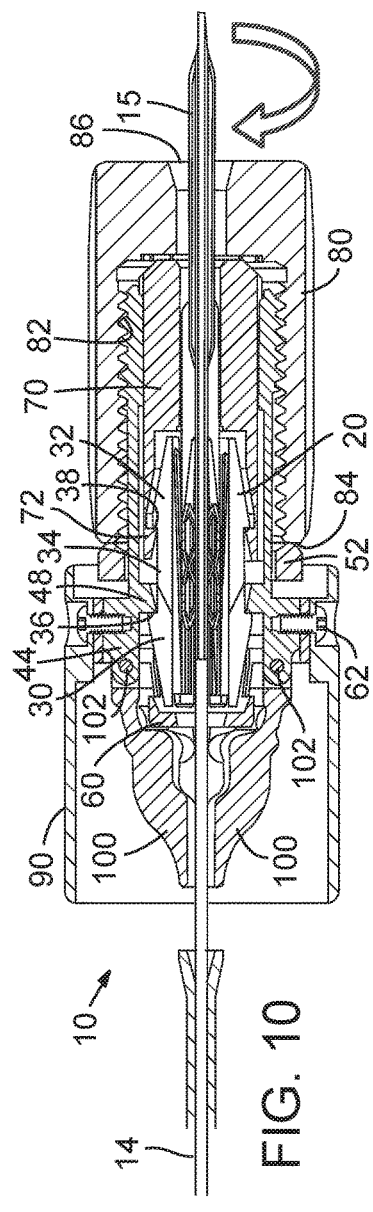
Figure 14:
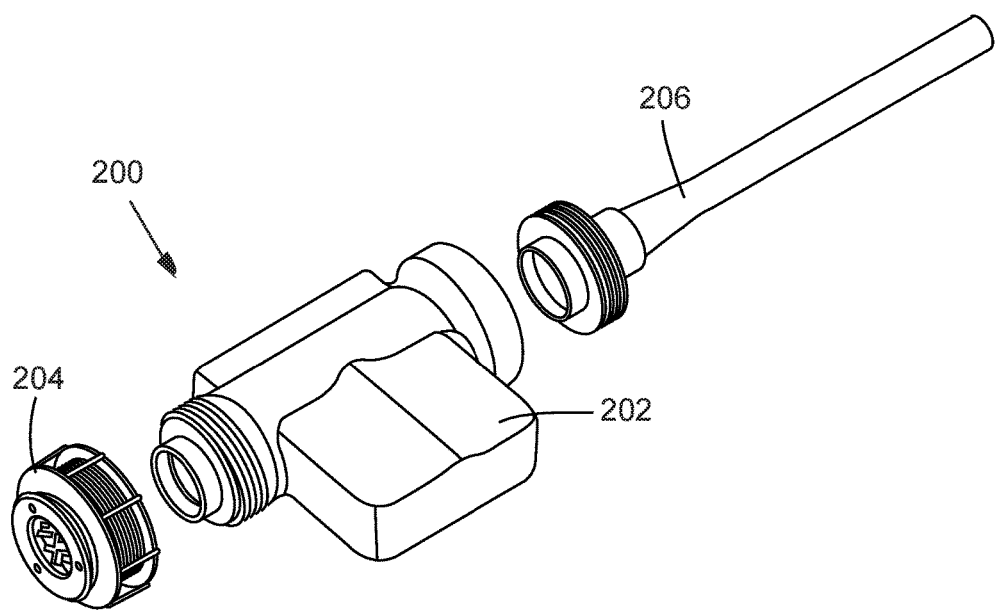
FIGS. 14-21C show alternative valve crimping systems disclosed herein.
Figure 15:
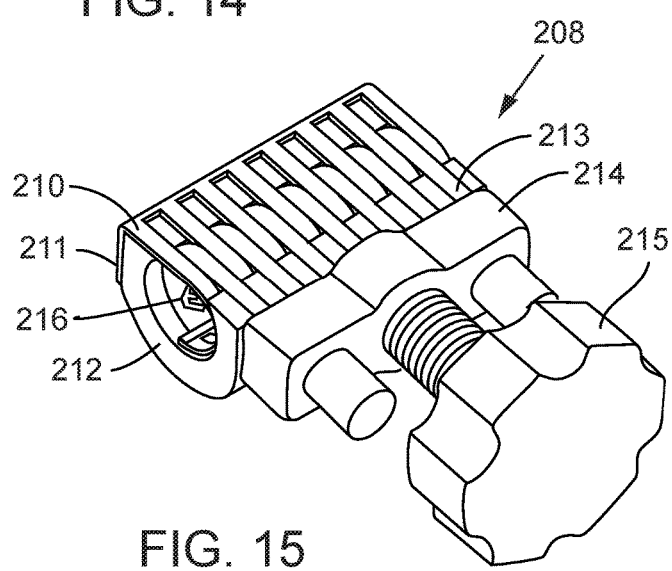
Figure 16:
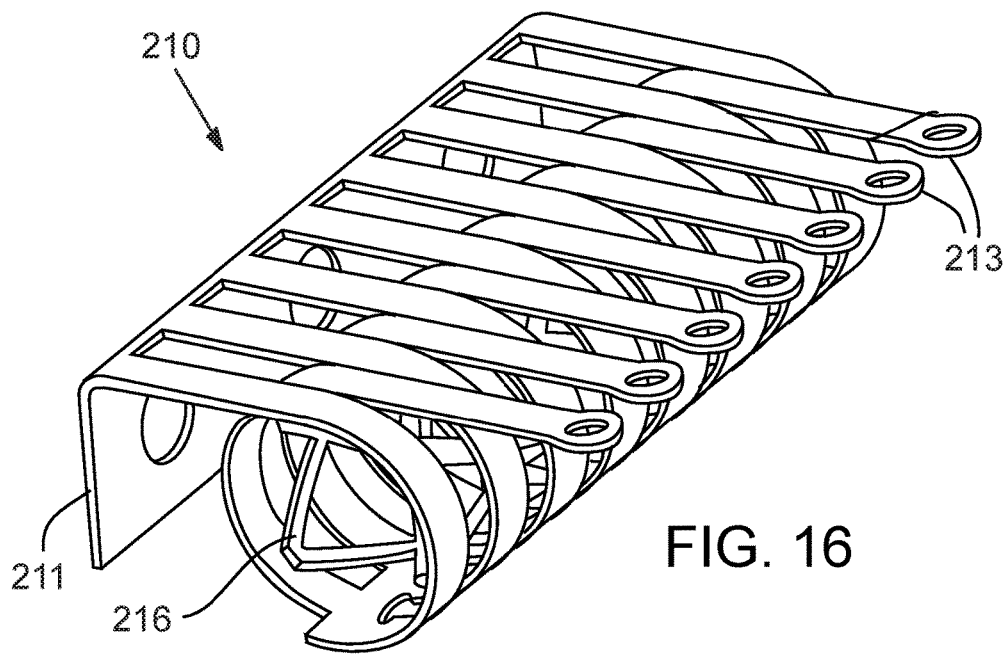
Figure 17:
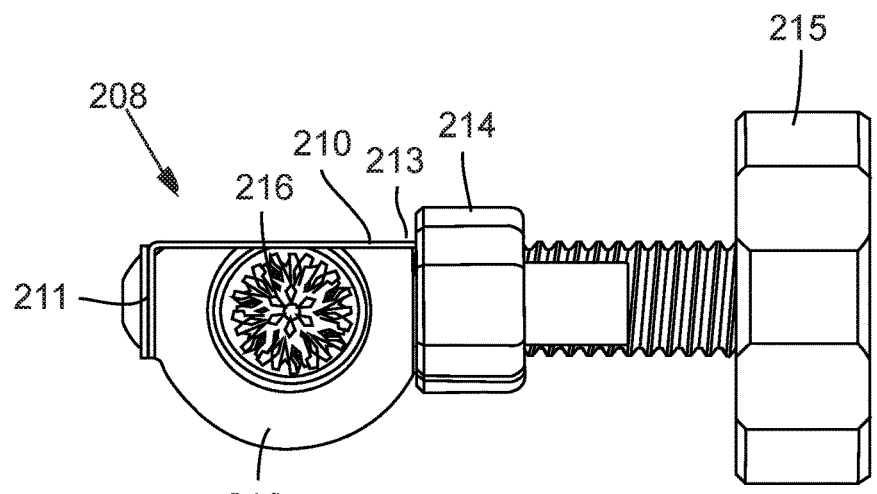

The crimping device 10 can further comprise a set of pushrods 50 positioned between the knob 80 and the jaws 100 that can provide the separation force needed to open the jaws 100, as shown in FIGS. 12 and 13. The pushrods 50 can be coupled in pairs by arched portions 52, as shown in FIG. 5, such that the pushrods can slide axially along the outer surface of the housing 40. The pushrods 50 can extend axially through apertures 46 in the flared end 44 of the housing and through apertures 64 in the stop 60, and can contact a distal surface of the jaws 100, as shown in FIG. 12. As the knob 80 rotates to compress the collet 20 and the valve 12, a proximal surface 84 of the knob moves distally toward the arched portions 52, as shown in FIGS. 8-10. When the proximal surface 84 of the knob contacts the arched portions 52, the pushrods 50 are urged proximally against the jaws 100, causing the jaws to pivot about the hinges 102 against the force of the spring 108 and releasing the jaws 100 from the delivery catheter 14, as shown in FIGS. 11 and 13.

FIG. 8 shows an initial configuration of the crimping device 10 with a valve 12 positioned within the collet 20 and a delivery catheter 14 extending axially through the device 10 and the valve 12. For example, this is the configuration the system can be in when the sterile package 16 is opened in the operating room when a physician is ready to deliver the valve into a patient. In this configuration, the valve 12 is premounted, but not fully crimped, at the desired location on the delivery catheter (a balloon catheter in the illustrated example) for delivery of the valve with final crimping to be performed by the physician just prior to implantation. In this manner, the physician need not perform the additional step of locating the valve at the desired location on the delivery catheter. In addition, because the valve can be packaged and sold in a precrimped configuration, the crimping device 10 is much smaller, lighter, and easier to use than conventional crimping devices that are designed to crimp a fully expanded valve.

In the initial configuration of FIG. 8, the collet 20 and the valve 12 are not under compression, or are under minimal compression, from the rest of the crimping device 10. As the knob 80 is rotated relative to the housing 40 (e.g., the doctor can grip the knob with one hand and the casing 90 with the other hand and twist them relative to each other), the knob 80 moves proximally relative to the housing 40 and urges the pusher 70 against the collet 20, pinching the collet between the internal annular ledges 48 and 72. As the knob 80 rotates and the distance between the ledges 48, 72 decreases, the ledges slide "up" the tapered surfaces of the end portions 30, 32, respectively, of the collet 20, causing the collet to compress radially.

FIG. 9 shows the crimping device at a fully crimped configuration wherein the ledges 48, 72 have slid all the way up the tapered end portions 30, 32 of the collet. In this configuration, the collet 20 is radially compressed to a furthest extent, compressing the valve 12 to a delivery configuration onto the catheter 14. The valve 12 can be crimped onto an inflatable balloon 15 of the delivery catheter, or crimped onto another portion of the delivery catheter that is just proximal to an inflatable balloon 15, as shown in FIG. 9, or distal to the balloon. In cases where the valve is mounted proximal or distal to the balloon, the valve can be repositioned onto the balloon for deployment after the valve and delivery catheter are inserted into the body. Examples of delivery catheters that can be used to introduce a valve into the vasculature of a patient in a position proximal or distal to a balloon are described in U.S. Patent Publication 2009/0281619, filed Oct. 8, 2008, which is incorporated herein by reference.

As shown in FIG. 10, additional rotation of the knob 80 in the same direction causes the ledges 48, 72 to slide over steps 36, 38, respectively, between the end portions 30, 32 and the intermediate portion 34 of the collet. As the ledges slide over the steps and into the intermediate portion 34, the collet 20 is allowed to radially expand a small amount, releasing compression on the valve 12. In addition, a clicking noise can be made as the ledges 48, 72 slide over the steps 36, 38, providing an audible indication for the doctor. In the case of a balloon expandable valve 12, the valve can remain in the delivery configuration while the collet 20 expands radially apart from the valve, releasing the valve enough to be slid axially out of the collet.

As shown in FIG. 10, the proximal end 84 of the knob 80 can contact the arched portions 52 of the pushrods 50 at the same time as, or just after, the ledges 48, 72 slide over the steps 36, 38 and the collet 20 is released. Further rotation of the knob 80 causes the knob 80 to push the pushrods 50 into the jaws 100, causing the jaws to pivot about the hinges 102 (as shown in FIGS. 11 and 13) and separate from the delivery catheter 14. At this point, the valve 12 is released from the collet 20 and the jaws 100 are released from the catheter 14, allowing the catheter with the valve mounted on it to be pulled proximally out of the crimping device 10, advanced distally through the device, or otherwise removed from the device.

In the embodiment shown in FIG. 3, for example, the valve 12 can be advanced through a distal outlet 86 of the crimping device 10 and into a loader 18 coupled to the distal end of the crimping device. The loader 18 can be a tubular structure configured to contain the valve 12 in the delivery configuration. The distal end of the loader 18 can be inserted into another device, such as an introducer sheath, which is already inserted into a patient, for percutaneous delivery of the valve 12 out of the loader 18 and into the patient.

FIGS. 14-17 show an alternative embodiment of a crimping device 200, which comprises a housing 202, a proximal end cap 204, and a distal loader 206. The housing 202 can contain a screw-actuated crimper 208 that comprises a coiled wire frame 210, a first end 211 of which is coupled to a first member 212 of the crimper and a second end 213 of which is coupled to a second member 214 of the crimper. Rotation of a screw knob 215 can move the second member 214 relative to the first member 212, thereby increasing or decreasing the diameter of the coiled wire frame 210, and thereby crimping or releasing a prosthetic valve 216 positioned within the coiled wire frame 210. A delivery catheter (not shown) can extend through the end cap 204 and through the valve 216 such that the valve can be crimped onto the delivery catheter. The delivery catheter with the valve 216 mounted thereon can then be retracted proximally out of the crimping device 200 or advanced through the crimping device, through the loader 206 and an introducer sheath, and into a patient.

Figure 18:
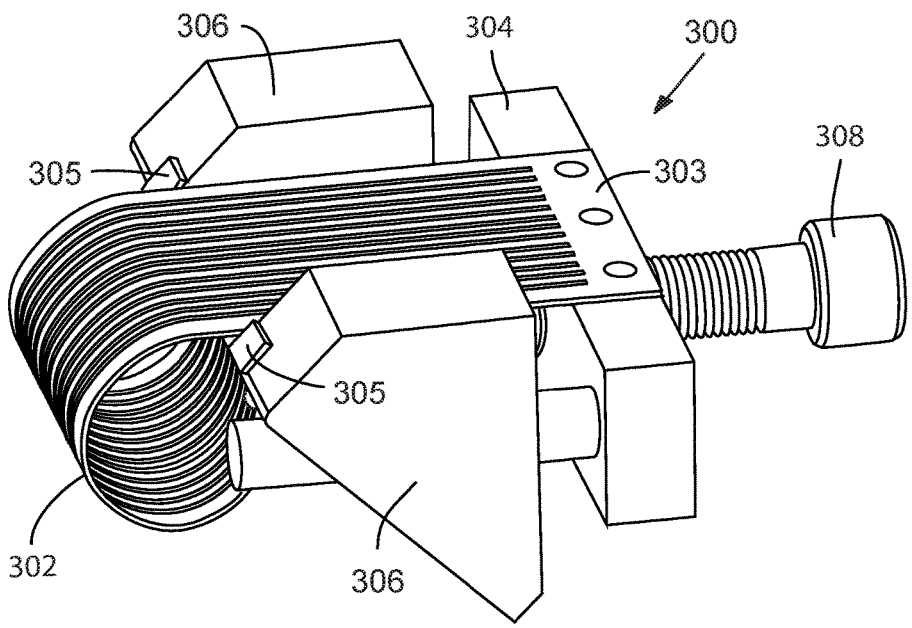
Figure 19:
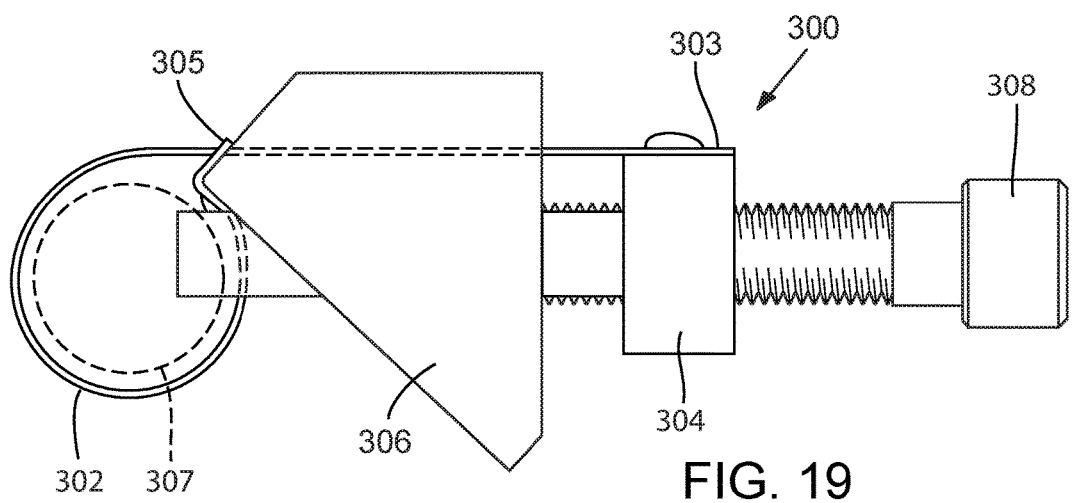

FIGS. 18 and 19 show another alternative embodiment of a crimping device 300, which comprises a coiled wire frame 302 coupled at a first end 303 to a first member 304 and coupled at a second end 305 to a second member 306. A valve 307 positioned within the wire frame 302 can be crimped by twisting a screw knob 308, which changes the diameter of the wire frame 302 by moving the first member 304 relative to the second member 306. The crimping device 300 can be used to crimp the valve 307 onto a delivery catheter (not shown) prior to insertion into a patient.

Figure 20:
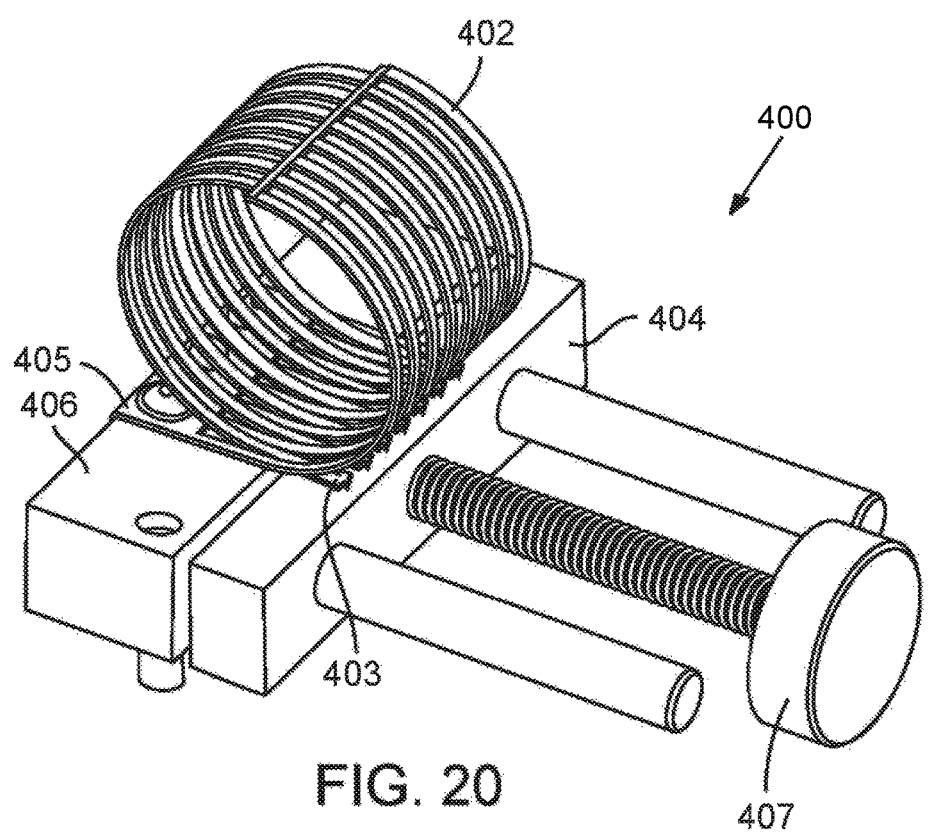

FIG. 20 shows another alternative embodiment of a crimping device 400, which comprises a coiled wire frame 402 coupled at a first end 403 to a first member 404 and coupled at a second end 405 to a second member 406. A valve (not shown) positioned within the wire frame 402 can be crimped by twisting a screw knob 407, which changes the diameter of the wire frame 402 by moving the first member 404 relative to the second member 406. The crimping device 400 can be used to crimp a valve onto a delivery catheter prior to insertion into a patient.

Each of the crimping devices 200, 300 and 400 can be pre-assembled in a sterile package with a valve positioned within the device. At least part of a delivery catheter can also be pre-assembled with the crimping devices 200, 300, 400 within a sterile package.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A crimping device for crimping a radially expandable and compressible prosthetic valve, the crimping device comprising:
    a collet configured to receive a prosthetic valve in a radially expanded state;
    a housing member configured to receive the collet;
    a pusher member that is movable relative to the collet;
    a rotatable knob coupled to the housing member and the pusher member, wherein when the knob is rotated relative to the housing member, the knob pushes the pusher member axially over the collet, which applies a radial force against the collet to cause radial crimping of the prosthetic valve.

2. The crimping device of claim 1, wherein the knob is threadably engaged to the housing member such that rotation of the knob causes the knob to move axially over the housing member.

3. The crimping device of claim 2, wherein the housing member comprises an internally tapered surface and further wherein rotation of the knob causes the pusher member to move closer to the tapered surface, which results in relative axial movement between the tapered surface and the collet.

4. The crimping device of claim 2, wherein the knob has internal threads that engage external threads of the housing member.

5. A method for crimping a prosthetic valve, the method comprising:

rotating a rotatable knob of a crimping device relative to a housing member of the crimping device to radially compress a prosthetic valve from an expanded or partially crimped configuration to a delivery configuration.

6. The method of claim 5, wherein rotation of the knob advances the prosthetic valve out of an outlet of the crimping device.

7. The method of claim 6, wherein rotation of the knob causes the knob to move axially relative to the housing member.

8. The method of claim 6, further comprising moving the prosthetic valve in the delivery configuration into a sheath of a delivery apparatus.

9. A crimping device for crimping a radially expandable and compressible prosthetic valve, the crimping device comprising:
   a housing member configured to house at least a portion of a prosthetic valve;
   a pusher member axially movable relative to the housing member wherein axial movement of the pusher member relative to the housing member is effective to compress the prosthetic valve from an expanded or partially crimped configuration to a delivery configuration; and
   a rotatable knob that is threadably engaged and rotatable relative to the housing member, wherein the pusher member is received in the knob such that rotation of the knob relative to the housing member causes axial movement of the pusher member relative to the housing.

10. The crimping device of claim 9, wherein the pusher member includes a generally cylindrical external surface that is received within the housing member.

11. The crimping device of claim 9, wherein the housing member comprises an internally tapered surface and further wherein the pusher member, when moved axially upon rotation of the knob, moves closer to the tapered surface to cause relative axial movement between the tapered surface and the prosthetic valve.

12. The crimping device of claim 11, wherein the pusher member includes a pusher internal annular ledge and further wherein rotation of the knob causes relative axial movement between the tapered surface and the pusher internal annular ledge.

13. The crimping device of claim 9, further comprising a sterile package containing a delivery catheter, the crimping device and the prosthetic valve.

14. The crimping device of claim 13, wherein the prosthetic valve is pre-assembled in a partially crimped configuration within the crimping device and within the sterile package.

15. The crimping device of claim 9, wherein the knob has internal threads that engage external threads of the housing member.

16. A method for crimping a prosthetic valve, the method comprising:
   rotating a rotatable knob of a crimping device relative to a housing member of the crimping device, wherein the rotatable knob is threadably engaged with the housing member, and wherein the crimping device includes a pusher member inside the housing;
   wherein rotating the rotatable knob causes the pusher member to move axially relative to the housing, thereby radially compressing a prosthetic valve in the housing from an expanded or partially crimped configuration to a delivery configuration.

17. The method of claim 16, further comprising after radially compressing the prosthetic valve to the delivery configuration, moving the prosthetic valve into a sheath of a delivery apparatus.

18. The method of claim 16, wherein the pusher member includes a generally cylindrical external surface that is received within the housing member.

19. The method of claim 16, wherein the knob extends co-axially over the housing member and has internal threads that engage external threads of the housing member.

20. The method of claim 16, wherein prior to rotating the rotatable knob, removing a delivery catheter, the crimping device and the prosthetic valve from a sterile package.

* * * * *